(12) United States Patent
Auclair

(10) Patent No.: US 9,956,200 B2
(45) Date of Patent: May 1, 2018

(54) COMPOSITIONS COMPRISING DIHYDROQUERCETIN FOR USE IN METHODS FOR TREATING THE EFFECTS ASSOCIATED WITH SKIN INFLAMMATORY DISORDERS

(71) Applicant: BIONOOX SUISSE SA, Cadempino (CH)

(72) Inventor: Christian Auclair, Saint-Arnoult-en-Yvelines (FR)

(73) Assignee: BIONOOX SUISSE SA, Cadempino (CH)

( * ) Notice: Subject to any disclaimer, the term of this patent is extended or adjusted under 35 U.S.C. 154(b) by 0 days. days.

(21) Appl. No.: 15/119,426

(22) PCT Filed: Feb. 18, 2015

(86) PCT No.: PCT/EP2015/053444
§ 371 (c)(1),
(2) Date: Aug. 17, 2016

(87) PCT Pub. No.: WO2015/124644
PCT Pub. Date: Aug. 27, 2015

(65) Prior Publication Data
US 2017/0246141 A1  Aug. 31, 2017

(30) Foreign Application Priority Data
Feb. 18, 2014 (EP) ................... 14155651

(51) Int. Cl.
| A61K 31/353 | (2006.01) |
| A61K 31/355 | (2006.01) |
| A61K 31/045 | (2006.01) |
| A61K 9/06 | (2006.01) |
| A61K 9/00 | (2006.01) |

(52) U.S. Cl.
CPC .......... *A61K 31/353* (2013.01); *A61K 9/0014* (2013.01); *A61K 9/06* (2013.01); *A61K 31/045* (2013.01); *A61K 31/355* (2013.01)

(58) Field of Classification Search
None
See application file for complete search history.

(56) References Cited

U.S. PATENT DOCUMENTS

| 9,585,822 B2* | 3/2017 | Lewis, II | A61K 8/347 |
| 2005/0249761 A1 | 11/2005 | Buenger et al. | |
| 2011/0097391 A1* | 4/2011 | Grigor'ev | A61K 9/107 424/450 |
| 2013/0295036 A1* | 11/2013 | Philippov | A61Q 19/00 424/74 |

FOREIGN PATENT DOCUMENTS

| EP | 2700413 A1 | 2/2014 |
| FR | 2963556 A3 | 2/2012 |
| JP | H07223933 A | 8/1995 |
| JP | 2000026263 A | 1/2000 |
| RU | 2382635 C1 | 2/2010 |
| WO | 03084553 A1 | 10/2003 |
| WO | 03051287 A2 | 3/2006 |
| WO | 2014029780 A1 | 2/2014 |

OTHER PUBLICATIONS

Kamatou, G. et al., J. Am. Oil Chem. Soc. 2010 vol. 87 pp. 1-7.*
Kirchner et al. "Flavonoids and 5-aminosalicylic acid inhibit the formation of neutrophil extracellular traps." Mediators of Inflammation, vol. 138, No. 7, 2013:710239, 2013.
Bito et al. "Flavonoids differentially regulate IFN gamma-induced ICAM-1 expression in human keratinocytes: molecular mechanisms of action." FEBS Letters, vol. 520, No. 1-3, 2002, pp. 145-152.
Zhu et al. "Anti-inflammatory constituents from Inula japonica." Zhongguo Zhongyao Zazhi, vol. 39, No. 1, 2014, pp. 38, abstract.
Wang et al. "Prevention of macrophage adhesion molecule-1 (Mac-1)-dependent neutrophil firm adhesion by taxifolin through impairment of protein kinase-dependent NADPH oxidase activation and antagonism of G protein-mediated calcium influx." Biochemical Pharmacology, vol. 67, No. 12, 2004, pp. 2251-2262.
Breinholt and Dragsted. "Structure-cytotoxicity relationships for dietary flavonoids." In vitro and Molecular Toxicology, vol. 11, No. 2, 1998, pp. 193-206.
Micali et al. "Use of an anti-inflammatory cream in childhood psoriasis (Poster)." 5th European Congress on Psoriasis & 7th International Psoriasis Symposium, 1998, Abstract book, p. 159.
Kadir and Barry. "alpha-Bisabolol, a possible safe penetration enhancer for dermal and transdermal therapeutics." International Journal of Pharmaceutics, vol. 70, No. 1-2, 1991, pp. 87-94.
Mizutani, K., et al, "Seitai no Sanka to Kosankaseibun no. Kaihatsu to Oyo", Fragrance Journal, vol. 25, No. 4, 1997, pp. 81-87 (with English Abstract).
English Translation of Japanese Office Action issued in Application 2015-527894, dated May 9, 2017.

* cited by examiner

*Primary Examiner* — Heidi Reese
(74) *Attorney, Agent, or Firm* — Young & Thompson

(57) ABSTRACT

A method of using a composition including dihydroquercetin, as well as optionally α-tocopherol and/or bisabolol, for treating the effects associated with skin inflammatory disorder, such as those associated with diseases characterized by inappropriate immune response, such as psoriasis, atopic dermatitis and/or urticaria. A process of manufacturing the composition is also described.

18 Claims, 3 Drawing Sheets

COMPOSITIONS COMPRISING DIHYDROQUERCETIN FOR USE IN METHODS FOR TREATING THE EFFECTS ASSOCIATED WITH SKIN INFLAMMATORY DISORDERS

FIELD OF INVENTION

The present invention relates to the use of a composition comprising dihydroquercetin, as well as optionally α-tocopherol and/or bisabolol for treating the effects associated with skin inflammatory disorder, such as those associated with diseases characterized by inappropriate immune response, such as psoriasis, atopic dermatitis and/or urticaria. The present invention also relates to a process of manufacturing the composition of the invention.

BACKGROUND OF INVENTION

Psoriasis

Psoriasis is a common skin disease characterized by thickened patches of inflamed, red skin covered with thick, silvery scales. Psoriasis occurs in a variety of forms that differ in their intensity, duration, location, shape and pattern of scales. The elbows and knees are the most common areas affected by psoriasis. It often appears in the same place on both sides of the body. The patches can range in size from smaller than a coin to larger than a hand. The most common forms of psoriasis are plaque psoriasis, the most common form, characterized by raised, inflamed, red lesions covered with a silvery-white buildup of dead skin cells (scales) and primarily found on the trunk, elbows, knees, scalp and finger or toe nails; pustular psoriasis, a rare form characterized by small pustules (whitehead-like lesions) found all over the body or confined to the palms, soles and other isolated areas of the body; guttate psoriasis, occurring most frequently in children and characterized by numerous small, red, drop-like scaly macules that develop rapidly over a wide area of skin, and inverse psoriasis, occurring in the armpit, under the breast, in skin folds, around the groin, in the cleft between the buttocks and around the genitals, which lacks the thick scale seen in other forms of psoriasis.

Psoriasis can be classified as mild, moderate, or severe. Mild psoriasis is considered to be scaling over less than 5-10 percent of the body, moderate psoriasis is considered to be scaling over 10 to 20 percent of the body and severe psoriasis is considered to be scaling over 20 percent of the body. In 5 percent of all psoriasis sufferers, arthritis will develop. This condition is called psoriatic arthritis. Arthritis is inflammation of a joint, usually accompanied by pain, swelling and changes in joint structure.

Psoriasis is a chronic and relapsing inflammatory disease of the skin associated with various immunologic abnormalities. Approximately 30% of psoriasis patients also have joint involvement, indicative of psoriatic arthritis. Genes and environment play a key role in the pathogenesis of these diseases: genome-wide linkage scans have notably revealed some overlap with psoriasis and atopic dermatitis susceptibility loci.

Many types of cells, including lymphocytes, dendritics APCs (antigen presenting cells), NKT (natural killer T) cells, neutrophils, mast cells, keratinocytes and fibroblasts are supposedly involved in the pathogenesis of psoriasis. Chronic psoriasis is in particular characterized by prominent skin infiltration by neutrophils and microabscess formation. IL-8 was found to be expressed in the neutrophils of psoriasis, suggesting a role for IL-8 in the formation of the microabcesses and pustules. Further, several studies suggest that increased levels of IL-8 expressed in both neutrophils and keratinocytes of psoriatic plaques play a contributing role in the migration of mast cells to lesion sites, the number of which is drastically increased at sites of psoriatic inflammation. Considering their role of multifactorial immune effector cells, mast cells are thus believed to play an essential role in perpetuating the inflammatory process of psoriasis. IL-17 and IL-23 are also known to play a major role in the psoriasis pathogenesis. It has in particular been demonstrated that mast cells and neutrophils are the predominant cell types containing IL-17 in human skin. Furthermore, IL-23 and IL-1β were found to induce mast cell extracellular trap formation and degranulation of human mast cells, suggesting a central role of IL-17 release in the pathogenesis of psoriasis.

Known psoriasis treatments may generally be classified in 3 major categories: topical treatments, systemic treatments and ultraviolet (UV) light therapy.

Topical treatments include emollients, such as creams, ointments, petrolatum, paraffin and hydrogenate vegetable oils, which reduce scaling; salicylic acid, which softens scales, facilitate their removal and increases adsorption of other topical agents; coal tar preparations, which are anti-inflammatory and decrease keratinocyte hyperproliferation; anthralin, which is a topical antiproliferative and anti-inflammatory agent; corticosteroids, which may be used topically or injected; vitamin D3 analogs, that induce normal keratinocyte proliferation and differentiation; calcineurin inhibitors; and tazarotene, a topical retinoid.

Systemic treatments include treatments with methotrexate; systemic retinoids (e.g., acitretin, isotretinoin), which are indicated for severe and recalcitrant cases of psoriasis vulgaris, pustular psoriasis and hyperkeratoticpalmoplantar psoriasis; immunosuppressants, such as Cyclosporineis; and immunomodulatory agents, such as TNF-α inhibitors (etanercept, adalimumab, infliximab), the T-cell modulator alefacept and Ustekinumab, a human monoclonal antibody that targets IL-12 and IL-23.

Finally, UV light therapy is typically used in patients with extensive psoriasis. Whereas the corresponding mechanism of action remains unknown, UVB light reduces DNA synthesis and can induce mild systemic immunosuppression. Further, a treatment (PUVA) also combines the administration of methoxypsoralen, a photosensitizer, with exposure to long-wave UVA light (330 to 360 nm): this results in an antiproliferative effect and also helps to normalize keratinocyte differentiation. Combined administration of retinoids and exposure to UV light, exposure to single NBUVB light (311 to 312 nm) or exposure to single excimer laser (308-nm) are also known methods for treating psoriasis.

Atopic Dermatitis

Atopic dermatitis, also currently known under the names "atopic eczema", "neurodermitis" or "prurigo Besnier" is a type of inflammatory, relapsing and pruritic skin disorders, the causes of which remain unknown. Atopic dermatitis may affect any part of the body, while being preferably localized on the hands and feet, on the ankles, wrists, face, neck and upper chest. Symptoms may vary but usually comprise red, inflamed and itchy rash and can develop into raised and painful bumps. Atopic dermatitis generally occurs together with other atopic diseases like hay fever, asthma and allergic conjunctivitis, and is often confused with psoriasis. The skin of patients with atopic dermatitis reacts abnormally and easily to irritants, food and environmental allergens.

Although there is no cure known for atopic dermatitis, treatments recommended for psoriasis may provide short-time alternatives for patients.

Urticaria

Urticaria, commonly referred to as "hives", is characterized by pale red, raised, itchy bumps. Causes for urticaria may be from allergic but also from non-allergic origins, and usually remain unknown. The majority of chronic hives cases have an idiopathic origin, caused by an autoimmune reaction. The underlying molecular mechanism possibly consists in the release of histamine or of cytokines from cutaneous mast cells, thereby resulting in fluid leakage from superficial blood vessels, such as capillaries leakage in the dermis. The edema formed persists until the interstitial fluid is adsorbed into the surrounding cells. To this day, no curative treatment is known. Antihistamines, such as diphenhydramine or tricyclic antioxydepressants, such as doxepin, may be used in therapy, also involving side effects. Corticosteroids such as prednisone are used for treating severe outbreaks and topical creams such as hydrocortisone, fluocinonide or desonide may also be prescribed for relieving itching.

WO 03/051287 discloses a composition for reducing, treating or preventing at least one adverse effect of ionizing radiation by topical application, said composition comprising a mixture of at least one non-flavonoid antioxidant and at least one flavonoid and wherein at least one component is obtained from green tea. The exemplified composition of patent application WO 03/05187 comprises quercetin as flavonoid and a mixture of vitamin A, vitamin E acetate, ascorbyl palmitate and lipoic acid as non-flavonoid antioxidant. The patients self-evaluated the effects of the administration of this composition and noted less severe radiation dermatitis after radiation therapy.

US2005/249761 relates to a topical composition for the prophylaxis and/or treatment of skin diseases and/or inflammation reactions of the skin and can also be used for the cosmetic care of the skin. This composition comprises aryl oxime and bisabolol, and may further include adjuvants and/or excipients. Aryl oximes are known to be useful for the treatment of skin inflammation but are difficult to formulate. In US patent application US2005/249761, it was shown that the use of bisabolol enables their stabilization while reinforcing the anti-inflammatory action. However, no evaluation of the efficacy of this composition is provided.

Kirchner et al (Mediators of inflammation, 2013, 2013: 710239) describes that flavonoids, including (+)-catechin hydrate, inhibit the production of reactive oxygen species (ROS) and the formation of neutrophil extracellular traps (NETs). In particular, this article discloses the role of NETs and NET components in autoimmune diseases such as psoriasis. However, Kirchner et al does not disclose the use of compositions comprising dihydroquercetin for treating the effects associated with skin inflammatory disorders.

Bito et al (FEBS Letters, 2002, 520(1-3):145-152) discloses the inhibition of IFNγ-induced ICAM-1 protein and mRNA expression by taxifolin in human keratinocytes. Bito et al thus suggests the therapeutic potential of taxifolin in skin pathological conditions. However, Bito et al fails to disclose any skin pathological conditions. In particular, Bito et al does not mention diseases characterized by inappropriate immune response, such as psoriasis, atopic dermatitis and/or urticaria.

Patent application No. EP12181058.4 discloses companion cosmetic treatments for assisting patients in the management of their therapy-related cutaneous discomfort. This application in particular describes cosmetic compositions comprising dihydroquercetin, α-tocopherol and bisabolol for treating the discomfort resulting from skin irritation, inflammation or cutaneous erythema that are provoked by a treatment, and preferably those resulting from anticancer radiotherapies and/or chemotherapy. Patent application No. EP12181058.4 nevertheless fails to disclose the use of compositions comprising dihydroquercetin for treating the effects associated with skin inflammatory disorders, and more particularly with diseases characterized by inappropriate immune response, such as psoriasis, atopic dermatitis and/or urticaria.

Even though several treatments are proposed for treating psoriasis, atopic dermatitis and/or urticaria, none of these treatments actually provide remedies which could both alleviate the effects associated with these diseases over mid- to long-term, and which would be devoid of deleterious secondary effects.

There is thus a need to provide solutions for treating the effects associated with skin inflammatory disorders, and more particularly with diseases characterized by inappropriate immune response, including skin inflammation, psoriasis, atopic dermatitis and/or urticaria. The present invention aims at reaching this need, and relates to the use of compositions suitable for being administered topically to patients.

Advantageously, the compositions of the invention are safe, do not contain phototoxic and/or photosensibilizing components, show no toxicity. They are also effective in treating the effects associated with skin inflammation and associated with diseases characterized by inappropriate immune response, such as psoriasis, atopic dermatitis and/or urticaria.

The composition of the invention presents the advantage to have a high stability and preservability. Moreover, the composition of the invention produces a pleasant feeling when applied on skin.

SUMMARY

The present invention thus concerns a composition comprising dihydroquercetin for use in a method for treating the effects associated with skin inflammatory disorders.

In an embodiment, the composition for use in the invention further comprises bisabolol.

In an embodiment, the composition is for use in a method for treating the effects associated with diseases characterized by inappropriate immune response, such as psoriasis, atopic dermatitis and/or urticaria.

In a specific embodiment of the invention, the composition further comprises α-tocopherol.

In a particular embodiment, the composition for use in the invention is such that the concentration of dihydroquercetin ranges from 1% to 10%, preferably from 3% to 9%, preferably from 5% to 7% w/w in weight of the total weight of the composition. In a particular embodiment, the composition of the invention is such that the concentration of bisabolol ranges from 0.1% to 1%, preferably from 0.3% to 0.7% w/w in weight of the total weight of the composition. In a particular embodiment, the composition of the invention is such that the concentration of α-tocopherol ranges from 0.5% to 2%, preferably from 1% to 1.5% w/w in weight of the total weight of the composition.

In a particular embodiment, the composition for use in the invention comprises or consists in dihydroquercetin, the concentration of which ranges from 1% to 10%, preferably from 3% to 9%, preferably from 5% to 7% w/w in weight of the total weight of the composition; bisabolol, the concentration of which ranges from 0.1% to 1%, preferably from 0.3% to 0.7% w/w in weight of the total weight of the composition and α-tocopherol, the concentration of which ranges from 0.5% to 2%, preferably from 1% to 1.5% w/w in weight of the total weight of the composition.

In an embodiment, the composition for use in the invention further comprises a cosmetically acceptable vehicle, preferably comprising at least one compound selected from the group comprising animal fat, vegetable fat, higher alcohols, glycols or a mixture of thereof.

In an embodiment, the composition for use in the invention further comprises at least one component selected from the group comprising surfactants, pigments, stabilizers, emollients, humectants or a mixture of thereof.

In an embodiment, the composition for use in the invention is a cream, a gel, an ointment, a solution, an emulsion, a mask, a milk, a lotion, a serum, a paste, a foam or a suspension, and preferably a cream.

In a particular embodiment, the composition for use in the invention is designed for topical administration.

The present invention further concerns a process of manufacturing the composition for use in the invention, said process comprising a step of blending DHQ, α-tocopherol and bisabolol with a cosmetically acceptable vehicle. In a particular embodiment, the process of manufacturing the composition for use in the invention, comprises a first step of blending DHQ in an oil, and further adding bisabolol. In a particular embodiment, the process of manufacturing the composition for use in the invention, comprises a first step of blending DHQ in an oil, and further adding bisabolol and α-tocopherol.

FIGURES

FIG. 1 is a graph showing the inhibitory effect of DHQ on the cytochrome c reduction (superoxide Anion production) resulting from the neutrophils activation by PMA or fMLP. Cytochrome c reduction is expressed in dDO/min. DHQ concentration is reported in μM. Numerical data corresponding to the graph of FIG. 1 are detailed in table I.

Figure 4:
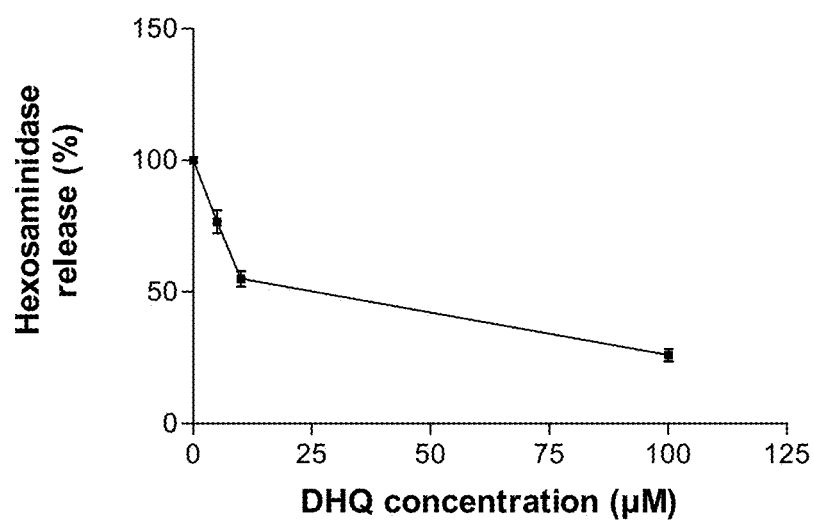

FIG. 4 is a graph showing the effect of DHQ on mast cell degranulation as estimated by beta-hexosaminidase release. Decrease of released beta-hexaminidase is expressed in percents, with 100% corresponding to the beta-hexaminidase release in absence of DHQ. Concentration of DHQ is reported in μM.

Figure 5:
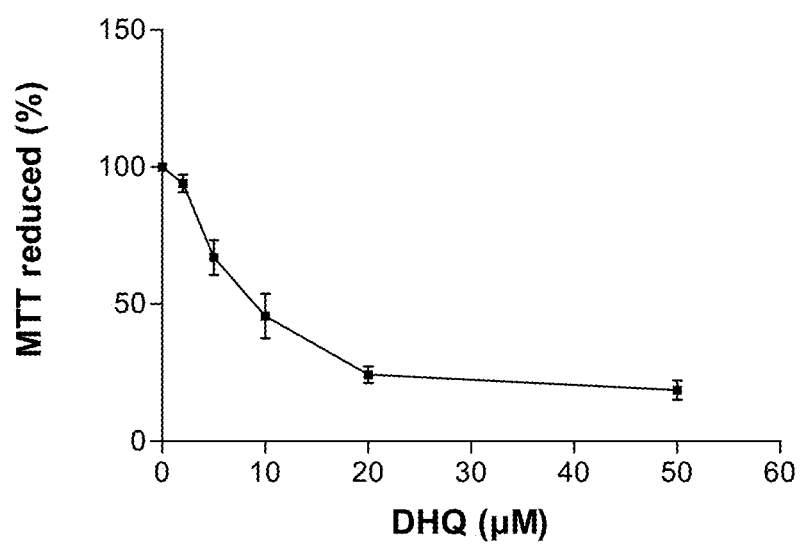

FIG. 5 is a graph showing the inhibition of Fibroblasts proliferation in the presence of increasing concentrations of DHQ as estimated by the decrease of reduced MTT levels. Decrease of reduced MTT levels is evaluated by measure of reduced formazan. Cell viability is assessed by the extent of MTT reduced. Concentration of DHQ is reported in μM.

DEFINITIONS

In the present invention, the following term has the following meaning:

"about" preceding a figure means plus or less 10% of the value of said figure.

"cosmetically acceptable" refers to a component that is suitable for use in contact with the skin without undue adverse side effects (such as toxicity, irritation, allergic response, and the like).

"vehicle" refers to a substance with which the component of interest is mixed or wherein the component of interest is dissolved. In an embodiment, the vehicle may be a cosmetically acceptable base.

"cosmetically acceptable base" refers to a cosmetically acceptable vehicle comprising a lipophilic component.

"treating" refers to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. In one embodiment, "treating" refers to reducing or alleviating at least one adverse effect or symptom of skin inflammatory disorders associated with a deficiency in or absence of an organ, tissue or cell function. A subject or mammal is successfully "treated" for an infection if, after receiving a therapeutic amount of an antibody according to the methods of the present invention, the patient shows observable and/or measurable reduction in or absence of one or more of the following: reduction in the number of pathogenic cells; reduction in the percent of total cells that are pathogenic; and/or relief to some extent, one or more of the symptoms associated with the specific disease or condition; reduced morbidity and mortality, and improvement in quality of life issues. The above parameters for assessing successful treatment and improvement in the disease are readily measurable by routine procedures familiar to a physician. In one embodiment, the term "treating" means "alleviating".

"companion cosmetic composition" refers to a cosmetic composition intended to assist patients in the management of their therapy-related cutaneous discomfort.

"subject" refers to a mammal, preferably a human. In one embodiment, a subject may be a "patient", i.e. a warm-blooded animal, more preferably a human, who/which is awaiting the receipt of, or is receiving medical care or was/is/will be the object of a medical procedure, or is monitored for the development of a skin inflammatory disorder. In one embodiment, the subject is an adult (for example a subject above the age of 18). In another embodiment, the subject is a child (for example a subject below the age of 18). In one embodiment, the subject is a male. In another embodiment, the subject is a female.

DETAILED DESCRIPTION

This invention relates to a composition comprising dihydroquercetin (DHQ) for use in a method for treating the effects associated with skin inflammatory disorders, and preferably those associated with diseases characterized by inappropriate immune response, more preferably psoriasis, atopic dermatitis and/or urticaria.

Dihydroquercetin (also referred to herein as "DHQ") is the common name of 3,3',4',5,7-pentahydroxyflavone dehydrate, also called 2-(3,4-dihydroxyphenyl)-3,5,7-trihydroxy-4H-1-benzopyran-4-one dehydrate, also known as taxifolin. DHQ is a natural compound of the flavonoid family. Flavonoids are reported to have therapeutic potentials because of their antioxidant, anti-inflammatory, anti-allergic or anti ischemic properties. Furthermore, flavonoids may penetrate into deep skin layers after topical application. Of these, quercetin is one of the most documented, but is known to be genotoxic, mutagen and with a low chemical stability.

DHQ is a valuable alternative to quercetin as it is characterized by a great chemical stability with conserved significant biological and pharmacological properties and by its safety. DHQ has been identified as a powerful antioxidant, as safe, and as a natural preservative. Therefore it has been marketed for 15-20 years as food supplement in Russia and in the US.

In a particular embodiment of the present invention, the concentration of DHQ in the composition for use in the invention ranges from 1% to 10% w/w (i.e. in weight, by weight of the total composition), preferably from 3% to 9% w/w, more preferably from 5% to 7% w/w, more preferably is about 6% w/w.

In a particular embodiment, the composition for us in the invention further comprises Bisabolol.

Bisabolol (6-methyl-2-(4-methyl-3-cyclohexen-1-yl)-5-hepten-2-ol, or 1-methyl-4-(1,5-dimethyl-1-hydroxyhex-4 (5)-nyl)cyclohexen-1) is a sesquiterperne that is found in various plants, including herbal tea and chamomile. The most important known effects of bisabolol are anti-inflammatory, wound healing, anti-bacterial, anti-mycotic and anti-phlogistic properties. Therefore it is widely used in cosmetic and personal care products. Especially, bisabolol may be used to enhance the transepidermal penetration, in other words it may be used to increase diffusivities across the modified skin barrier (Kadir et al., Int. J. Phann., 1991, 70:87-94). In the present invention, bisabolol is used as a vehicle of DHQ and/or α-tocopherol, since bisabolol is thought to facilitate the diffusion of DHQ and/or α-tocopherol to the dermal area. In one embodiment, DHQ is extracted from a type of larch wood, preferably from Siberian larch. In an embodiment, DHQ containing powder contains at least 96% w/w by weight of DHQ and corresponds to the technical requirements and sanitary rules on the basis of analytical and microbiological reports.

In an embodiment, the concentration of bisabolol in the composition of the ranges from 0.1% to 1% w/w in weight by weight of the total composition, preferably from 0.3% to 0.7% w/w, more preferably is about 0.5%.

Further, in a particular embodiment, the invention concerns a composition comprising DHQ, bisabolol and further comprising α-tocopherol for use in a method for treating the effects associated with skin inflammatory disorders, in particular those associated with various diseases characterized by inappropriate immune response, preferably psoriasis, atopic dermatitis and/or urticaria.

α-Tocopherol, commonly named "vitamin E", has many biological functions, the antioxidant function being considered as the most important one. Furthermore, it is lipid-soluble. It performs its function as antioxidant on connection with the glutathione peroxidase pathway and it protects cell membrane from oxidation by reacting with lipid radicals produced during the lipid peroxidation chain reaction. This process would remove the reactive free radical intermediates and prevent the oxidation chain reaction from continuing. The resulting α-tocopheroxyl radicals may be converted back to the reduced form through reduction by other oxidants such as ascorbate, retinol or ubiquinol, as well as DHQ. Without willing to be bound by a theory, it is the Applicant understanding that in the composition of the present invention, α-tocopherol favors the recycling of DHQ under its active phenolic form.

In an embodiment, the concentration of α-tocopherol in the composition for use in the invention ranges from 0.5% to 2% w/w in weight by weight of the total composition, preferably 1% to 1.5% w/w, more preferably is about 1.2% w/w.

In an embodiment, the composition for use in the invention comprises 1% to 10% in weight of the total weight of the composition of dihydroquercetin, 0.5% to 2% w/w of α-tocopherol, 0.1% to 1% w/w of bisabolol, and a cosmetically acceptable vehicle.

In an embodiment, the composition for use in the invention comprises 3% to 9% in weight of the total weight of the composition of dihydroquercetin, 1% to 1.5% w/w of α-tocopherol, 0.3% to 0.7% w/w of bisabolol, and a cosmetically acceptable vehicle.

In an embodiment, the composition for use in the invention comprises 6% in weight of the total weight of the composition of dihydroquercetin, 1.2% w/w of α-tocopherol, 0.5% w/w of bisabolol, and a cosmetically acceptable vehicle.

The inventors have discovered that the specific combination of DHQ, bisabolol and α-tocopherol unexpectedly alleviates the effects associated with skin inflammatory disorders and more particularly those associated with various diseases characterized by inappropriate immune response, preferably psoriasis, atopic dermatitis and/or urticaria.

By "effects associated with skin inflammatory disorders", "effects associated with diseases characterized by inappropriate immune response", or "effects associated with psoriasis, atopic dermatitis and/or urticaria", it is meant skin damages characterized by thickened patches of inflamed red skin covered with thick, silvery scales; raised inflamed red lesions covered with a silvery-white buildup of dead-skin cells (scales); small red drop-like scaly macules developing rapidly over a wide area of skin; red inflamed and itchy rash developing into raised and painful bumps; and pale red raised itchy bumps.

According to an embodiment, the composition for use in a method for treating the effects associated with skin inflammatory disorders further comprises a cosmetically acceptable vehicle.

In an embodiment, the vehicle is a cosmetically acceptable base.

According to an embodiment, the cosmetically acceptable base comprises at least one compound selected from the group comprising animal fat, vegetable fat, higher alcohols, glycols, mineral oil or a mixture thereof.

In an embodiment, animal fat is for example stearic acid. In an embodiment, vegetable fat is for example linoleic acid, jojoba oil (also called oil *simmondsia chinensis*), sweet almond oil, avocado oil or a mixture thereof. In an embodiment, higher alcohols are for example cetearyl alcohol. In an embodiment, glycols are for example propylene glycol. In an embodiment, mineral oil is for example paraffin oil.

According to an embodiment, the composition for use in a method for treating the effects associated with skin inflammatory disorders further comprises at least one component selected from the group comprising surfactants, pigments, stabilizers, emollients, humectants or a mixture of thereof.

In an embodiment, surfactants are for example PEG-100 stearate, PEG-20 stearate or a mixture thereof. In an embodiment, stabilizers are for example carbomer. In an embodiment, pigments are for example zinc oxide. In an embodiment, emollients are for example caprylic/capric triglyceride, dicapryl ether, glyceryl stearate, glyceryl monostearate or a mixture thereof. In an embodiment, humectants are for example glycerin, sorbitol or a mixture thereof.

According to an embodiment, the composition for use in a method for treating the effects associated with skin inflammatory disorders further comprises perfume, such as for example citronellol, geraniol, limonene, or a mixture thereof.

According to an embodiment, the composition for use in a method for treating the effects associated with skin inflammatory disorders further comprises water. In a specific embodiment, the composition for use in a method for treating the effects associated with skin inflammatory disorders is an oil-in-water emulsion.

According to an embodiment, the composition for use in a method for treating the effects associated with skin inflammatory disorders further comprises components that are commonly employed as a cosmetic base and that are known by the skilled artisan.

In an embodiment, the composition for use in a method for treating the effects associated with skin inflammatory disorders does not comprise any tar or sulfur derivatives such as steroids, vitamin D3 analogs, keratolytic agents, topical retinoids, artificial or genetically manipulated substances, known allergic agents, artificial coloring or scent agents.

In an embodiment, the composition for use in a method for treating the effects associated with skin inflammatory disorders is designed for topical administration.

According to an embodiment, the composition for use in a method for treating the effects associated with skin inflammatory disorders is under the form of a cream, a gel, an ointment, a solution, an emulsion, a mask, a milk, a lotion, a serum, a paste, a foam or a suspension. In a preferred embodiment, the composition for use in the invention is a cream.

In an embodiment, the composition for use in a method for treating the effects associated with skin inflammatory disorders is a cosmetic composition. In an embodiment, the composition for use in a method for treating the effects associated with skin inflammatory disorders is a pharmaceutical composition.

In an embodiment, the composition for use in a method for treating the effects associated with skin inflammatory disorders is a therapeutical composition.

In another embodiment, the composition for use in a method for treating the effects associated with skin inflammatory disorders is a non-therapeutical composition.

In an embodiment, the composition for use in a method for treating the effects associated with skin inflammatory disorders is not used as a companion cosmetic composition to prevent and/or alleviate the cutaneous discomfort induced by a therapy. In another embodiment, the composition for use in a method for treating the effects associated with skin inflammatory disorders is not used as a companion cosmetic composition for assisting patients in the management of their therapy-related cutaneous discomfort.

In an embodiment, the invention relates to the composition for use in a method for treating the effects associated with skin inflammatory disorders, wherein said method consists in the administration of the composition of the invention. Therefore, in a specific embodiment, said method does not comprise the administration of another treatment.

In another embodiment, the composition for use in a method for treating the effects associated with skin inflammatory disorders is administered in combination with another treatment for skin inflammatory disorders. In an embodiment, the composition for use in a method for treating the effects associated with skin inflammatory disorders is administered in combination with another known psoriasis treatment. Examples of known psoriasis treatments include, but are not limited to, topical treatments such as emollients, salicylic acid, anthralin, vitamin D3 analogs, calcineurin inhibitors, tazaroten; systemic treatments such as treatments with methotrexate, immunosuppressants, alefacept, ustekinumab; and ultraviolet (UV) light therapy.

In another embodiment, the composition for use in a method for treating the effects associated with skin inflammatory disorders is administered in combination with another known atopic dermatitis treatment. Examples of known atopic dermatitis treatments include, but are not limited to, treatments recommended for psoriasis as short-time alternatives.

In another embodiment, the composition for use in a method for treating the effects associated with skin inflammatory disorders is administered in combination with another known urticaria treatment. Examples of known urticaria treatments include, but are not limited to, antihistamines, tricyclic antioxydepressants, corticosteroids.

In one embodiment, the composition for use of the invention is administered in combination with a topically administered treatment. In another embodiment, the composition for use of the invention is administered in combination with an orally administered treatment.

In an embodiment, the composition for use in a method for treating the effects associated with skin inflammatory disorders is stable over one year in standard storage conditions.

In an embodiment, the use of the composition according to the invention is external. In an embodiment, the use of the composition according to the invention requires the composition to be applied on inflamed skin.

In an embodiment, an amount of composition is applied which is sufficient to cover the afflicted area of the skin with a thin layer of the composition.

In an embodiment, the composition should be rubbed into the skin until little or no residue remains on the skin. In one embodiment, the composition is applied on the skin into a regular massage. According to an embodiment, the composition may be applied one, two, three or more times a day.

In an embodiment, the composition used in the method of the invention is stored in a container, preferably a glass container. In an embodiment, the glass container is sterilized using a dry heat sterilizer. In an embodiment, the container is a plastic container. In an embodiment, the plastic container is sterilized using UV irradiation using low-pressure "Hard Quartz Glass" UV Lamps.

In an embodiment, the application of the composition of the invention allows the treatment of the effects associated with skin inflammatory disorders, and more particularly those associated with psoriasis, atopic dermatitis and/or urticaria.

The invention also relates to a method for treating the effects associated with skin inflammatory disorders, and preferably those associated with diseases characterized by inappropriate immune response such as psoriasis, atopic dermatitis and/or urticaria.

In one embodiment of the invention, the method for treating the effects associated with skin inflammatory disorders comprises the administration of the composition as described hereinabove. In a preferred embodiment, the method for treating the effects associated with skin inflammatory disorders comprises the step of applying on the skin of a patient in need thereof a composition according to the present invention.

In one embodiment, the patient is affected by skin inflammatory disorder. In a preferred embodiment, the patient is affected by a disease characterized by inappropriate immune response such as psoriasis, atopic dermatitis and/or urticaria. In another embodiment, the patient is at risk of being affected by skin inflammatory disorder.

In one embodiment, the patient was not treated previously with another treatment for skin inflammatory disorder. In another embodiment, the patient previously received one or more other treatments for skin inflammatory disorder.

The invention also relates to a process for manufacturing the composition for use in the invention. In an embodiment, the process of the invention comprises a step of blending DHQ, α-tocopherol and bisabolol with a cosmetically acceptable vehicle.

In an embodiment, the process of the invention comprises a preliminary step of dissolving DHQ in jojoba oil (Oil *Simmondsia chinensis*), sweet almond oil or avocado oil before blending DHQ, α-tocopherol and bisabolol with a cosmetically acceptable vehicle.

In an embodiment, the cosmetically acceptable vehicle is manufactured by any conventional method known in the art.

EXAMPLES

The present invention is further illustrated by the following examples. Examples are not intended to limit the scope of the present invention.

Example 1: Effect of DHQ on the Activation of Polymorphonuclear Neutrophils

Materials and Methods:

Neutrophils ($5 \times 10^5$) are suspended in 0.5 mL of Hanks balanced salt solution containing 10 μM luminol at 37° C. The cells are then stimulated with $10^{-6}$M fMLF (N-formylmethionyl-leucyl-phenylalanine). Chemiluminescence is recorded with a luminometer (Berthold-Biolumat LB937).

PMA (12-0-tetradecanoyl-phorbol-13-acetate, Consolidated Midland Corp., Brewster, N.Y.) is dissolved at 1 mg/ml in dimethyl sulfoxide. This stock solution maintains full biological activity for several months when stored at 25° C. in the dark. Unless otherwise specified, polymorphonuclear neutrophils (PMN), $10^6$/ml in BS—H, are put into plastic centrifuge tubes (Falcon No. 2070, Falcon Labware, Div. of Becton, Dickinson & Co., Oxnard, Calif.) and brought to 37° C. PMA stock solution is added to provide a final concentration of 100 ng/ml of PMA. "Resting" (control) cells are exposed to 1% (vol/vol) dimethyl sulfoxide. A chemiluminescence (using luminol) method is used to measure Reactive Oxygen species (ROS) production (Dang et al, J Clin Invest. 2006, 116(7):2033-43; Boussetta et al, Blood. 2010, 116(26):5795-802). Superoxide production is measured by the superoxide dismutase (SOD)-inhabitable ferricytochrome c reduction assay.

Results

Figure 1:
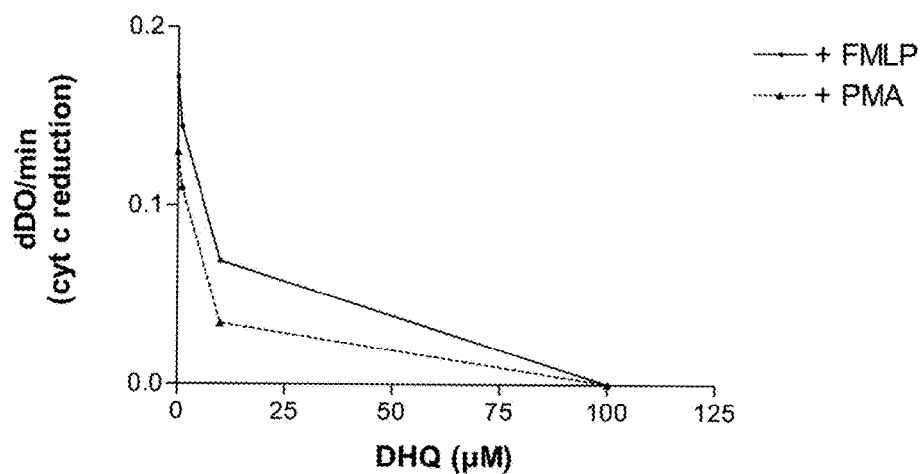

When activated by opsonized bacteria, zymozan, fMLP (Formyl-Methionyl-Leucyl-Phenylalanine) or PMA (phorbol myristate acetate), neutrophils undergo an oxidative burst resulting in the production of superoxide anion and subsequent hydrogen peroxide. The oxidative burst is mainly mediated by the NADPH oxidase activation, enzyme responsible of the superoxide anion production. The quantification of Superoxide anion by the measurement of the cytochrome c reduction (see table I below and FIG. 1) shows that the addition of DHQ strongly inhibits cytochrome c reduction. This effect results either from the direct anion superoxide scavenging or from the inhibition of NADPH oxidase activation.

TABLE I

Inhibitory effect of DHQ on the cytochrome c reduction (anion superoxide production) resulting from the neutrophils activation by PMA or fLMP.

| Neutrophils status: | Control | DHQ: 1 μM | DHQ: 10 μM | DHQ: 100 μM |
|---|---|---|---|---|
| Resting (dDO/min) | 0.004 | 0.000 | 0.036 | 0.086 |
| +fMLP (dDO/min) | 0.172 | 0.144 | 0.105 | 0.040 |
| +PMA (dDO/min) | 0.130 | 0.110 | 0.070 | 0.021 |

("dDO" stands for optic density variation)

In order to further investigate the effect of DHQ on the oxidative burst of neutrophils, ROS production was also measured by chemoluminescence for detecting both surperoxide anion and hydrogen peroxide.

Neutrophils are triggered by PMA (100 ng/mL) in the presence of different concentrations of DHQ (0, 1, 10 and 100 μM) at 37° C. in Hanks buffer containing 10 μM luminol and chemiluminescence is measured by a chemiluminometer. Total chemiluminescence counts during 22.21 min. (integrals) corresponding to total ROS production are determined. The corresponding results are presented in table II and FIG. 2.

TABLE II

Figure 2:
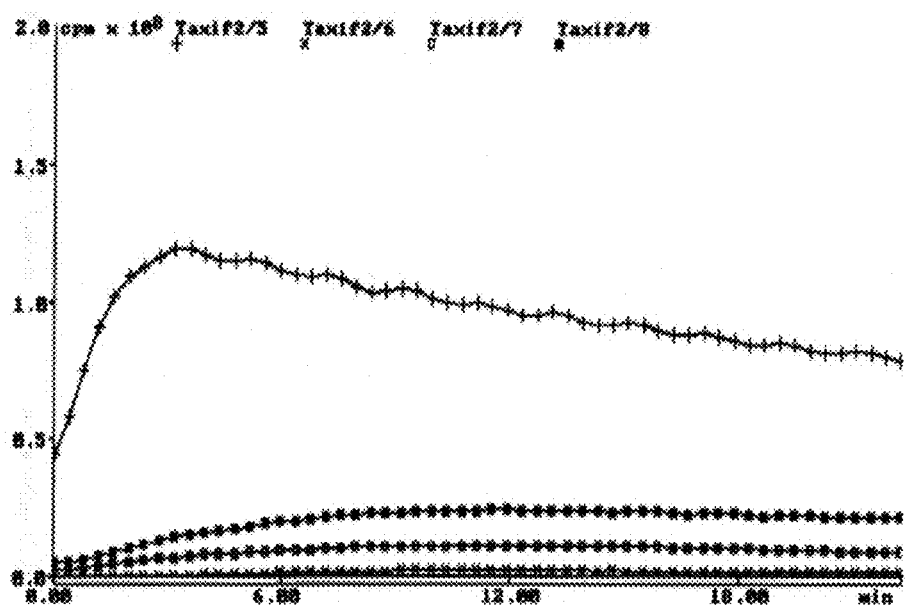
FIG. 2 is a graph showing the inhibitory effect of DHQ on the ROS production resulting from the neutrophils activation by 100 ng/ml PMA. Numerical data corresponding to the graph of FIG. 2 are detailed in table II.

ROS production by neutrophils triggered by PMA 100 ng/mL (experimental data corresponding to FIG. 2).

| Report Taxif2 | | 8 Samples | | Measuring Time: 22.21 min Integration Time: 0.00 to 22.21 min | | | | |
|---|---|---|---|---|---|---|---|---|
| Sample | Integral | Peak max cpm | Slope max cpm | T.Slope max | T.half (rise) | T.max (peak) | T.half (fall) | Smoot Facto |
|  | 2.150E+09 | 1.196E+08 | 6.991E+07 | 0.67 | 0.22 | 3.33 | > | 0 |
|  | 3.573E+07 | 2.260E+06 | 1.033E+06 | 4.66 | 4.89 | 11.55 | > | 0 |
|  | 2.072E+08 | 1.134E+07 | 4.380E+06 | 1.55 | 2.22 | 9.55 | > | 0 |
|  | 4.509E+08 | 2.430E+07 | 9.790E+06 | 1.78 | 2.44 | 11.77 | > | 0 |

Similarly, neutrophils were triggered by fMLP ($10^{-6}$ M) in the presence of different concentrations of DHQ (0, 1, 10 and 100 μM) at 37° C. in Hanks buffer containing 10 μM luminol and chemiluminescence was measured by a chemiluminometer. Total chemiluminescence counts during 22.21 min. (integrals) corresponding to total ROS production were determined. The corresponding results are presented in table III and FIG. 3.

Results

Mast cell degranulation was induced by sequential treatment of mast cell by IgE, then by anti-IgE antibodies. Degranulation was subsequently measured by evaluating the

TABLE III

Figure 3:
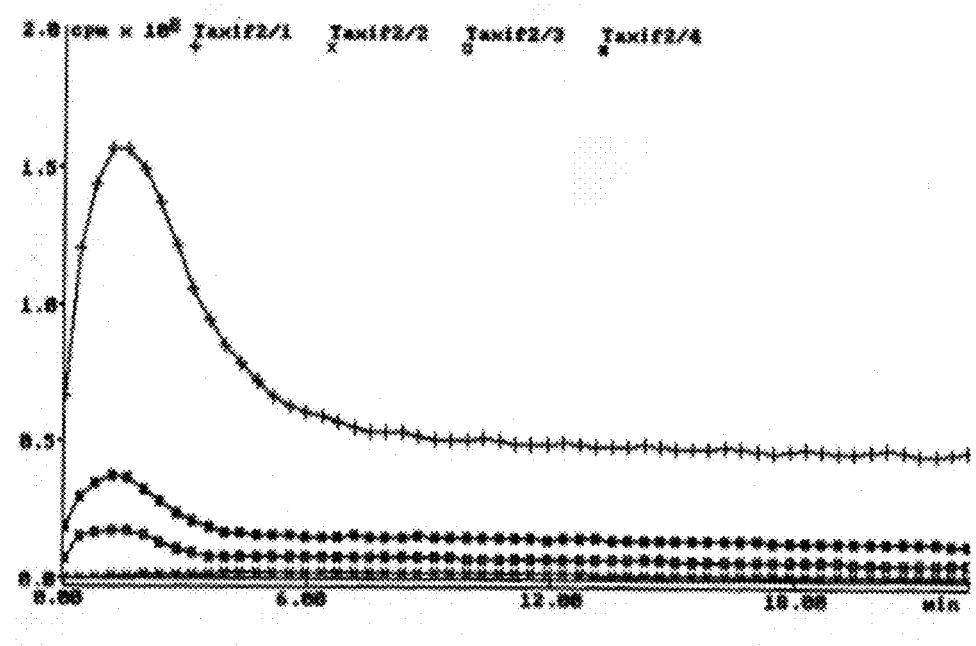
FIG. 3 is a graph showing the inhibitory effect of DHQ on the ROS production resulting from the neutrophils activation by $10^{-6}$ M fMLP. Numerical data corresponding to the graph of FIG. 3 are detailed in table III.

ROS production by neutrophils triggered by fMLP ($10^{-6}$M) (experimental data corresponding to FIG. 3).

|   | cpm | cpm | max | (rise) | (peak) | (fall) | Factor |
|---|-----|-----|-----|--------|--------|--------|--------|
| 1 | 1.453E+09 | 1.571E+08 | 9.691E+07 | 0.22 | < | 1.55 | 4.44 | 0 |
| 2 | 4.329E+07 | 2.533E+06 | 1.464E+06 | 2.00 | 1.55 | 6.00 | > | 0 |
| 3 | 1.867E+08 | 1.770E+07 | 1.206E+07 | 0.22 | < | 1.33 | 3.55 | 0 |
| 4 | 3.838E+08 | 3.731E+07 | 2.492E+07 | 0.22 | < | 1.33 | 3.78 | 0 |

| Report Taxif2 | 8 Samples | Measuring Time: 22.21 min Integration Time: 0.00 to 22.21 min |

| Sample | Integral | Peak max cpm | Slope max cpm | T.Slope max | T.half (rise) | T.max (peal) | T.half (fall) | Smoot Facto |
|---|---|---|---|---|---|---|---|---|
| 1 | 1.453E+09 | 1.571E+08 | 9.691E+07 | 0.22 | < | 1.55 | 4.44 | 0 |
| 2 | 4.329E+07 | 2.533E+06 | 1.464E+06 | 2.00 | 1.55 | 6.00 | > | 0 |
| 3 | 1.867E+08 | 1.770E+07 | 1.206E+07 | 0.22 | < | 1.33 | 3.55 | 0 |
| 4 | 3.838E+08 | 3.731E+07 | 2.492E+07 | 0.22 | < | 1.33 | 3.78 | 0 |

The chemiluminescent assay detected all oxidizing ROS including the protonated form of superoxide anion and hydrogen peroxide.

The results of FIGS. 2 and 3 show that DHQ strongly inhibits the ROS production by neutrophils activated either by PMA or fMLP. The inhibitory effect provided by DHQ appears very efficient since the addition of 1 μM in the assay medium results in around 80% inhibition of the ROS production in both experiments.

These results thus suggest that DHQ, in addition to its well-known antioxidant property, inhibits the NADPH oxidase activation in polymorphonuclear neutrophils triggered by either fMLP or PMA. This property is confirmed by the fact that DHQ further strongly inhibits the oxygen consumption of polymorphonuclear neutrophils triggered by PMA and fMLP (data not shown).

Example 2: Effect of DHQ on the Activation of Mast Cells

Materials and Methods:

Pure populations of human mast cells (HMC) are obtained by long-term culture of human normal hematopoietic progenitors ($CD34^+$ cells) in the continuous presence of Stem Cell Factor (SCF). Sources of these $CD34^+$ cells are mainly bone marrow, cord blood or peripheral blood. Usually, mononuclear cells from bone marrow and cord blood contain 0.5-1% of $CD34^+$ cells, whereas peripheral blood contains less than 0.1% of $CD34^+$ cells.

Hematopoietic progenitor cells can be rapidly and efficiently enriched to a purity of about 85-98% using positive selection of magnetically labeled $CD34^+$ cells. Hematopoietic progenitor cells are then magnetically labeled using MACS CD34 MicroBeads. The magnetically labeled cells are enriched on positive selection columns in the magnetic field. Mononuclear cells from peripheral blood (PBMC), cord blood, or bone marrow may otherwise be obtained by density gradient centrifugation over Ficoll Paque®. Fractionation methods for producing mast cells are described in the art (see for instance Arock et al., 2008, Methods in Molecular biology 415: 241-254).

release of beta-hexosaminidase, 1 h after IgE stimulation (see FIG. 4).

The experiments performed demonstrate that DHQ has a strong inhibitory activity on degranulation of mast cells (80% inhibition at 100 μM and up to 50% at 10 μM).

This result indicates that DHQ displays a high inhibitory activity, which is superior to kinase inhibitors and chromoglycate (reference molecule).

Example 3: Effect of DHQ on NIH-3T3 Fibroblasts Proliferation

Materials and Methods:

The NIH 3T3 cell line was purchased from the ATCC (CRL1658). Cell lines are grown in Dulbecco's Modified Eagles' Medium (DMEM) supplemented with 10% heat inactivated newborn calf serum, 100 UI/mL penicillin and 100 μg/mL streptomycin (all from Gibco BRL) at 37° C. in a humidified 5% $CO_2$ atmosphere. DHQ is dissolved in DMSO. Cells are cultured during 48 hours in the absence or in the presence of various DHQ concentrations. NIH-3T3 fibroblasts are immortalized cells which mimic the inflammatory phenotype assessed by the abundance of actin stress fibers and high contractility.

The effects of DHQ on the growth of NIH-3T3 cells are determined using the 3-(4,5-dimethylthiazol-2-yl)-2,5-diphenyltetrazolium bromide (MTT) assay. Briefly, cells are plated on 96 well plates at 4,000 cells per well with increasing DHQ concentrations. After 72 hours of incubation with the drug, medium is removed and replaced by complete medium+MTT (10% v/v). After 3 hours of incubation, formazan crystals are dissolved in buffer containing 10% SDS (w/v, Bio-Rad), 50% Dimethyl formamide (Sigma), pH 4.7. Absorbance of reduced formazan is measured at 580 nm. Results are presented in FIG. 5: 100% of MTT reduced is attributed to the measure performed in absence of DHQ.

Results

As shown in FIG. 5, cell viability of NIH-3T3 cells cultured in the presence of increasing DHQ concentrations is reduced (cell viability is assessed by the extent of MTT reduced). Considering that NIH-3T3 fibroblasts are immortalized cells which mimic the myofibroblasts phenotype, it can therefore be inferred from these results that fibroblast proliferation is inhibited in the presence of increasing concentrations of DHQ.

Example 4: Skin Cream Composition for Treating Psoriasis

Topical compositions comprising 1, 2, 5 or 10% w/w DHQ, 0.5 or 1% w/w α-tocopherol and 0.1 or 0.2% w/w bisabolol, jojoba oil and a cosmetically acceptable vehicle comprising water, paraffin oil, stearyl alcohol, glyceryl monostearate, dimethicone E 900 (silicone), PEG 20 stearate, PEG 100 stearate, *simmondsia* chinnensis oil, cetylic alcohol, imidazolin urea, butyl phenyl methylproprional, cinnamyl alcohol, citronellol, geraniol and limonene are prepared.

TABLE IV summary of the prepared topical compositions.

| | DHQ (% w/w) | α-tocophérol (% w/w) | bisabolol (% w/w) | base |
|---|---|---|---|---|
| Product 1 | 1 | 0.5 | 0.1 | qsp 100% |
| Product 2 | 1 | 0.5 | 0.2 | qsp 100% |
| Product 3 | 1 | 1 | 0.1 | qsp 100% |
| Product 4 | 1 | 1 | 0.2 | qsp 100% |
| Product 5 | 2 | 0.5 | 0.1 | qsp 100% |
| Product 6 | 2 | 0.5 | 0.2 | qsp 100% |
| Product 7 | 2 | 1 | 0.1 | qsp 100% |
| Product 8 | 2 | 1 | 0.2 | qsp 100% |
| Product 9 | 5 | 0.5 | 0.1 | qsp 100% |
| Product 10 | 5 | 0.5 | 0.2 | qsp 100% |
| Product 11 | 5 | 1 | 0.1 | qsp 100% |
| Product 12 | 5 | 1 | 0.2 | qsp 100% |

The said compositions are obtained by first blending DHQ with jojoba oil, sweet almond oil or avocado oil. Typically, when the composition contains 5% DHQ, 12.5% of Jojoba, sweet almond or avocado oil are used (in w/w to the weight of the topical composition). When the composition contains 2% DHQ, 5% of Jojoba, sweet almond or avocado oil are used (in w/w to the weight of the topical composition). When the composition contains 1% DHQ, 2.5% of Jojoba, sweet almond or avocado oil are used (in w/w to the weight of the topical composition).

The components of the cosmetic vehicle, α-tocopherol and bisabolol are then mixed with the mixture of DHQ and oil, by blending.

Example 5: Effect of Composition of Example 4 on the Skin of Patients Suffering Psoriasis The compositions of example 4 were tested in a clinical trial enrolling 5 patients, in a non-controlled unblind study.
Method
Patients were treated with the compositions of example 4. Protocol of the trial consisted in the application of the cream once a day on the inflamed skin area. The primary objective was to evaluate the treatment efficiency assessed by the objective measurement of the skin inflammation extent and patients self-evaluation. All patients included were men diagnosed for psoriasis.
Results
Reporting of the trial clearly shows at least a decrease of skin inflammation and in some cases a complete disappearance of the inflamed area. The observed effect remains significant several days after the discontinuation of the treatment.

The invention claimed is:

1. A method of treating a subject suffering from the effects associated with skin inflammatory disorders characterized by inappropriate immune response selected from the group consisting of psoriasis and urticarial, comprising administrating an effective amount of a composition comprising dihydroquercetin to the subject.

2. The method according to claim 1, wherein the concentration of dihydroquercetin in the composition ranges from 1% to 10% w/w in weight of the total weight of the composition.

3. The method according to claim 1, wherein the concentration of dihydroquercetin in the composition ranges from 3% to 9% w/w in weight of the total weight of the composition.

4. The method according to claim 1, wherein the concentration of dihydroquercetin in the composition ranges 5% to 7% w/w in weight of the total weight of the composition.

5. The method according to claim 1, wherein the composition further comprises bisabolol.

6. The method according to claim 1, wherein the composition further comprises bisabolol and wherein the concentration of bisabolol ranges from 0.1% to 1% w/w in weight of the total weight of the composition.

7. The method according to claim 1, wherein the composition further comprises α-tocopherol.

8. The method according to claim 1, wherein the composition comprises α-tocopherol and wherein the concentration of α-tocopherol ranges from 0.5% to 2% w/w in weight of the total weight of the composition.

9. The method according to claim 1, wherein the composition comprises dihydroquercetin, bisabolol and α-tocopherol.

10. The method according to claim 1, wherein the composition comprises dihydroquercetin, bisabolol and α-tocopherol, wherein the concentration of dihydroquercetin ranges from 1% to 10% w/w, wherein the concentration of bisabolol ranges from 0.1% to 1% w/w and wherein the concentration of α-tocopherol ranges from 0.5% to 2% w/w, in weight of the total weight of the composition.

11. The method according to claim 1, wherein the composition further comprises a cosmetically acceptable vehicle.

12. The method according to claim 1, wherein the composition further comprises a cosmetically acceptable vehicle and wherein the cosmetically acceptable vehicle comprises at least one compound selected from the group consisting of animal fat, vegetable fat, higher alcohols, glycols, and a mixture thereof.

13. The method according to claim 1, wherein the composition further comprises at least one component selected from the group consisting of surfactants, pigments, stabilizers, emollients, humectants, and a mixture thereof.

14. The method according to claim 1, wherein the composition is a cream, a gel, an ointment, a solution, an emulsion, a mask, a milk, a lotion, a serum, a paste, a foam or a suspension.

15. The method according to claim 1, wherein the composition is a cream.

16. The method according to claim 1, wherein the composition is designed for topical administration.

17. The method according to claim 1, wherein the effective amount of the composition is administrated topically to the subject.

18. The method according to claim 1, wherein the method consists of the administration of the composition to the subject.

* * * * *